United States Patent
Gao et al.

(10) Patent No.: US 10,436,722 B2
(45) Date of Patent: Oct. 8, 2019

(54) POSITIVE/NEGATIVE PHASE SHIFT BIMETALLIC ZONE PLATE

(71) Applicant: University Of Science And Technology Of China, Hefei, Anhui (CN)

(72) Inventors: Kun Gao, Anhui (CN); Jian Chen, Anhui (CN); Renfang Hu, Anhui (CN); Zhili Wang, Anhui (CN); Dajiang Wang, Anhui (CN); Zhiyun Pan, Anhui (CN); Wangsheng Chu, Anhui (CN); Shiqiang Wei, Anhui (CN)

(73) Assignee: University of Science And Technology of China, Hefei, Anhui (CN)

( * ) Notice: Subject to any disclaimer, the term of this patent is extended or adjusted under 35 U.S.C. 154(b) by 506 days.

(21) Appl. No.: 15/311,879

(22) PCT Filed: May 22, 2014

(86) PCT No.: PCT/CN2014/078122
§ 371 (c)(1),
(2) Date: Nov. 17, 2016

(87) PCT Pub. No.: WO2015/176272
PCT Pub. Date: Nov. 26, 2015

(65) Prior Publication Data
US 2017/0082560 A1    Mar. 23, 2017

(51) Int. Cl.
*G02B 27/00*    (2006.01)
*G01N 23/083*    (2018.01)
(Continued)

(52) U.S. Cl.
CPC .......... *G01N 23/083* (2013.01); *B05D 1/005* (2013.01); *C23F 1/00* (2013.01); *G02B 5/18* (2013.01);
(Continued)

(58) Field of Classification Search
CPC .......... G02B 27/44; G21K 1/06; G21K 1/067; G21K 7/00
See application file for complete search history.

(56) References Cited

U.S. PATENT DOCUMENTS

| | | | |
|---|---|---|---|
| 2004/0020892 A1 | 2/2004 | Matthews et al. | |
| 2014/0204463 A1* | 7/2014 | Harada | G21K 1/06 359/565 |
| 2015/0091756 A1* | 4/2015 | Casciato | H01Q 3/20 342/377 |

FOREIGN PATENT DOCUMENTS

| | | |
|---|---|---|
| CN | 1710449 A | 12/2005 |
| CN | 101430428 A | 5/2009 |
| WO | WO-2010019354 A1 | 2/2010 |

OTHER PUBLICATIONS

"International Application No. PCT/CN2014/078122, International Search Report dated Feb. 27, 2015", w/ English Translation, (dated Feb. 27, 2015), 8 pgs.

(Continued)

*Primary Examiner* — Dani Fox
(74) *Attorney, Agent, or Firm* — Schwegman Lundberg & Woessner, P.A.

(57) ABSTRACT

The invention provides a positive/negative phase shift bimetallic zone plate and production method thereof, wherein the positive/negative phase shift bimetallic zone plate comprises: a first metallic material having a positive phase shift; a second metallic material having a negative phase shift at a working energy point; wherein the first metallic material and the second metallic material are alternately arranged, so that the second metallic material replaces the blank portion in a cycle of a traditional zone plate.

10 Claims, 2 Drawing Sheets

(51) Int. Cl.
   *G02B 5/18*     (2006.01)
   *B05D 1/00*     (2006.01)
   *C23F 1/00*     (2006.01)
   *G21K 1/06*     (2006.01)
   *G02B 27/44*    (2006.01)
   *G21K 7/00*     (2006.01)

(52) U.S. Cl.
   CPC .............. *G02B 27/44* (2013.01); *G21K 1/06* (2013.01); *G21K 1/067* (2013.01); *G21K 7/00* (2013.01)

(56) References Cited

OTHER PUBLICATIONS

"International Application No. PCT/CN2014/078122, Written Opinion dated Feb. 27, 2015", (dated Feb. 27, 2015), 4 pgs.
Reinspach, J., et al., "13nm high-efficiency nickel-germanium soft x-ray zone plates", J. Vac. Sci. Technol. B, vol. 29, No. 01, (Jan. 5, 2011), 4 pgs.
Tamura, Shigeharu, "Multilayer Fresnel Zone Plate with High-Diffraction Efficiency: Application of Composite Layer to X-ray Optics", Metal, Ceramic and Polymeric Composites for Various Uses edited by: Dr. John Cuppoletti, (Jul. 2011), 19 pgs.

* cited by examiner

POSITIVE/NEGATIVE PHASE SHIFT BIMETALLIC ZONE PLATE

PRIORITY APPLICATIONS

This application is a U.S. National Stage Filing under 35 U.S.C. 371 from International Application No. PCT/CN2014/078122, filed on 22 May 2014, and published as WO2015/176272 on 26 Nov. 2015; which application and publication are incorporated herein by reference in its entirety.

TECHNICAL FIELD

The invention relates to the field of X-ray microscopic imaging, in particular, to a positive/negative phase shift bimetallic zone plate.

BACKGROUND

A zone plate is one of the conventional optical elements for diffraction, and is often used to focus an X-ray and act as an objective lens of an imaging system. In fact, a zone plate is a circular optical element for diffraction, which consists of concentric zones, which have radially increasing linear densities and represent alternate bright and dark as shown in FIG. 1). According to the Fresnel's diffraction theory, if a circular aperture is divided to zones in series in accordance with the formula $r_n = \sqrt{n\lambda f}$ (n: serial number of a zone, $\lambda$: wavelength; f: focal length), and the odd zones or even zones are shielded, a Fresnel zone plate will thus configured. The zones forming the zone plate is referred to as half-wave zones, wherein the difference between the optical paths from the focal point to arbitrary two adjacent half-wave zones is $\lambda/2$. This means that the light waves through two adjacent half-wave zones have a phase difference of $\pi$ when they arrive the focal point, and destructive interference will occur at the focal point. Hence, a zone plate consists of alternate transparent and opaque half-wave zones, so as to achieve the purpose of constructive interference. If opaque half-wave zones in a zone plate are replaced by transparent half-wave zones having a phase shift of Π, a transparent half-wave zone having an optical path of $\lambda/2$ will be made, and thus the light waves through two adjacent half-wave zones have a phase difference of either 0 or $2\pi$, when they arrive the focal point, and all of the light passing through the zone plate will form constructive interference at the focal point, which is the theory of normal phase type zone plates. [See *Synchrotron Radiation Light Source and Application Thereof*, final volume, p. 686]

The two most important parameters of a zone plate are the outermost zone width and the zone thickness. The spatial resolution ($\Delta$) of a zone plate imaging system is determined by the outermost zone width ($dr_N$) of the zone plate, by $\Delta = 1.22 dr_N$. In a certain extension, the diffraction efficiency of a zone plate is improved with increasing zone thickness. However, an important factor that limits the development of zone plates is the ratio of the height to the width. There is a conflict between the outermost zone width and the zone thickness in a zone plate due to the processing technology, among other factors. Currently, either the outermost zone width of a zone plate cannot be smaller, or the efficiency of the high resolution zone plate cannot be very high. Therefore, there is a bottleneck in the spatial resolution of zone plate imaging systems (hard X-ray: 30 nm; water window: 10 nm).

The refractive index of a substance may be represented as $n = 1 - \delta + 1\beta$, wherein $\delta$ is a phase term, $\beta$ is an absorption term. At some certain energies, $\delta$ and $\beta$ of a substance would change suddenly, and further, the phase term $\delta$ therein may have a negative value. Presence of a phase shift having a negative value possibly bring new breakthrough for the phase type zone plates, which are made by utilizing phase-shift characteristics of elements.

SUMMARY

In one aspect, an embodiment of the invention provides a positive/negative phase shift bimetallic zone plate, comprising:
a first metallic material having a positive phase shift;
a second metallic material having a negative phase shift at a working energy point;
wherein the first metallic material and the second metallic material are alternately arranged, so that the second metallic material replaces the blank portion in a cycle of a traditional zone plate.

In another embodiment of the invention, the positive/negative phase shift bimetallic zone plate is annular, and the first metallic material and the second metallic material form a structure of alternate rings.

In another embodiment of the invention, the first metallic material is often selected from nickel, gold, germanium, titanium, vanadium, chromium, manganese, iron, cobalt, copper, zinc, etc.

In another embodiment of the invention, the second metallic material is selected from titanium, vanadium, chromium, manganese, iron, cobalt, nickel, copper, zinc, gallium, germanium, hafnium, tungsten, rhenium and osmium, etc.

In another embodiment of the invention, in the case that the positive/negative phase shift bimetallic zone plate has the same thickness as that of a normal monometallic phase zone plate, the diffraction efficiency of the positive/negative phase shift bimetallic zone plate is higher than the diffraction efficiency of the normal monometallic phase zone plate.

In another embodiment of the invention, the positive/negative phase shift bimetallic zone plate is a novel vanadium-nickel bimetallic zone plate.

In another embodiment of the invention, the thickness of the positive/negative phase shift bimetallic zone plate is 10 to 500 nm, which varies according to different resolutions of the zone plate, and selects a thickness as high as possible when it is allowed by the processing condition.

In another embodiment of the invention, there is no hollow portion in the structure of the positive/negative phase shift bimetallic zone plate, which structure can avoid the problem of the probable collapse of normal zone plates.

In another embodiment of the invention, the efficiency of the positive/negative phase shift bimetallic zone plate directly relates to the zone thickness, and the diffraction efficiency of the zone plate is improved with increasing zone thickness in a certain range. For a high resolution (no more than 30 nm) plate, the height of the ring cannot be very high due to the restriction of the ratio of height to width, and thus the diffraction efficiency is limited.

In another embodiment of the invention, the working energy of the positive/negative phase shift bimetallic zone plate is defined at different energy points, according to different zone plate materials. The reason thereof is that negative phase shifts of different metals exist in different narrow energy sections (a few ells).

In another aspect, an embodiment of the invention provides a method of producing a positive/negative phase shift bimetallic zone plate, comprising following steps:

a. depositing a thin film of a first metallic material on a substrate;

b. forming a photoresist having a zone plate structure on the thin film of the first metallic material;

c. transferring the zone plate structure to the thin film of the first metallic material by performing etching via the forming photoresist having the zone plate structure, so as to form a zone plate structure of the first metallic material;

d. depositing the second metallic material at interspaces formed by the etching;

e. removing the photoresist, so as to form a positive/negative phase shift bimetallic zone plate structure.

In another embodiment of the invention, the photoresist is coated by spin coating, and thereafter is subjected to electron beam exposure, so as to form a photoresist having a zone plate structure.

In another embodiment of the invention, the etching in step d is performed by argon ion etching and various reactive ion etchings.

In another embodiment of the invention, further comprising:

opening a window on the back side of the positive/negative phase shift bimetallic zone plate structure obtained in step e, to obtain the positive/negative phase shift bimetallic zone plate.

DETAILED DESCRIPTION

The invention proposes a novel phase type zone plate, which can achieve two effects: 1) being able to reduce the metal thickness required when the maximum first-order diffraction efficiency is achieved, and 2) improving the diffraction efficiency of a zone plate without increasing the ring height. The main novel and inventive point is the use of a structure with two alternate metals to replace traditional monometallic zone plates, wherein one metal has a positive phase shift and the other metal has a negative phase shift at a working energy point. We name it as a "positive/negative phase shift bimetallic zone plate".

Figure 1:
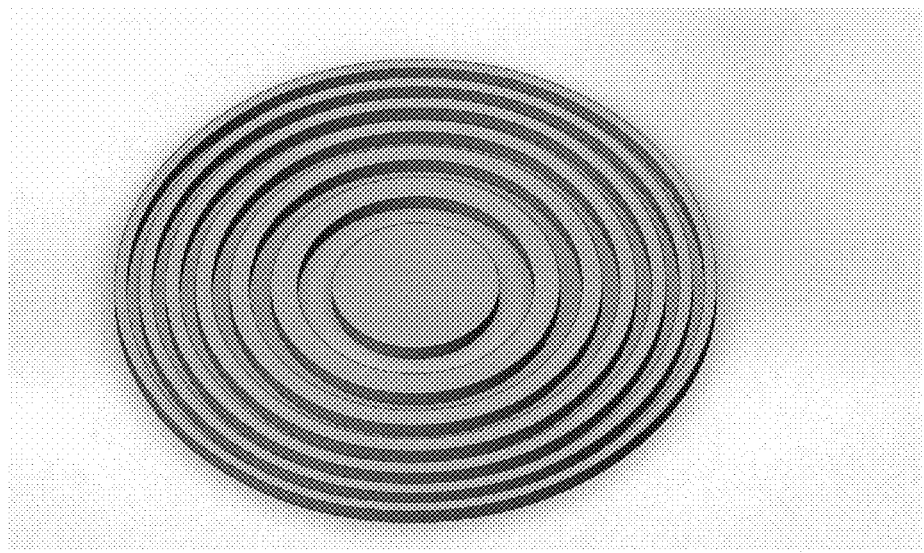
FIG. 1 is a schematic structure drawing of a conventional zone plate.
Figure 2:
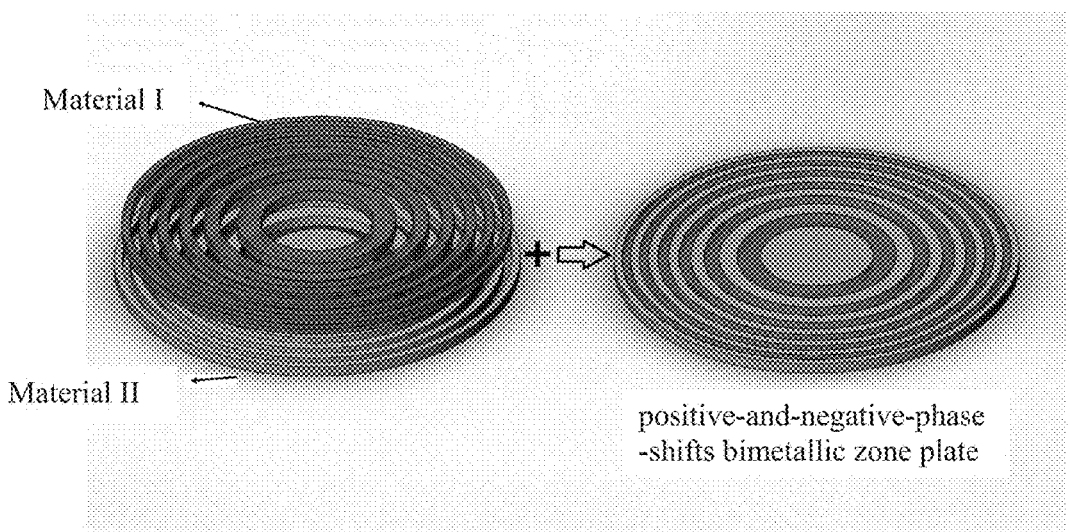
FIG. 2 is a schematic structure drawing of a positive/negative phase shift bimetallic zone plate.

In contrast to traditional zone plates, we use another material to replace the blank portion in a cycle of a traditional zone plate, wherein the selected material for the replacement needs to have a negative phase shift at the working energy point. Thus, the material thickness, which is required when the phase difference caused by adjacent zones is $\pi$, can be reduced, and thereby the difficulty of producing the zone plate is reduced. The structure of the novel zone plate is shown in FIG. 2, wherein the radii of the zones are also calculated by the formula $r_n = \sqrt{n\lambda f}$ (n: serial number of a zone, $\lambda$: wavelength; f: focal length). In contrast to the traditional zone plate shown in FIG. 1, structurally, a material having a negative phase shift at the working energy is added in FIG. 2, wherein the material having negative phase shift can be either of the materials in the structural drawing.

Most of metals have a negative phase shift at certain energy. These energy points are referred to as "working energy point" herein. For example, metal, such as titanium (453 eV), vanadium (512 eV), chromium (574 eV), manganese (638 eV), iron (706 eV), cobalt (778 eV), nickel (852 eV), copper (932 eV), zinc (1022 eV), gallium (1116 eV), germanium (1217 eV), hafnium (1661 eV), tungsten (1809 eV), rhenium (1883 eV), osmium (1960 eV), or the like, would have a negative phase shift near a corresponding energy. Theoretically, all of these metals can be used to produce positive/negative phase shift bimetallic zone plates working at different energies.

According to calculation, as compared to traditional monometallic phase type zone plate, the metal thickness, which is required when the peak value of the first-order diffraction efficiency is achieved, is lower, in the case of the positive/negative phase shift bimetallic zone plate, and the positive/negative phase shift bimetallic zone plate can keep the efficiency peak value thereof corresponding to the efficiency peak value in a monometallic case. Therefore, we realized that the high efficiency is remained while the difficulty of producing the zone plate is reduced. In addition, the efficiency of a positive/negative phase shift bimetallic zone plate is higher than that of a normal zone plate, when the thicknesses of the zone plates are the same (in the case that the resolution is better than 150 nm). Therefore, the invention can effectively improve diffraction efficiency of fine zone plates.

Taking a novel vanadium-nickel bimetallic zone plate as an example, at an energy of 511.9 eV, a conventional nickel zone plate achieves the maximum first-order diffraction efficiency of 22% at a thickness of about 250 nm, while the novel zone plate proposed by the invention achieve the maximum first-order diffraction efficiency of 24% at a thickness of only 140 nm. The thickness of a zone plate can be reduced to about 56% of the previous one. Currently, the nickel metallic phase type zone plate used in water window, which is produced superiorly in the world, can achieve an outermost zone width of 13 nm and a ring height of 35 nm [Towards 10-nm soft X-ray zone plate fabrication]. At an energy of 511.9 eV, the theoretical value of the first-order diffraction efficiency thereof is 1.6%, while the theoretical efficiency of the novel vanadium-nickel bimetallic zone plate having the same width and thickness can achieve 4.3%, increasing by near 170%.

Example

The zone plate proposed by the invention can be made by combining any metal having a negative phase shift at certain energy with another arbitrary metal.

A novel phase type zone plate of two metals, i.e. vanadium and nickel, is used as an example for illustration.

The metal vanadium represents a maximum negative phase shift at an energy of 511.9 eV, and this energy is just near the conventional "water window" energy, so we can use two metals, i.e. vanadium and nickel (a metal conventionally used in a "water window"), to produce a positive/negative phase shift bimetallic zone plate at the energy of 511.9 eV.

The first-order diffraction efficiency of a normal phase zone plate is [Phase zone plates for x rays and the extreme uv]:

$$Eff = \frac{1}{\pi^2}[1 + \exp(-2k\beta t) - 2\exp(-k\beta t)\cos(k\delta t)]$$

On the basis of above, the first-order diffraction efficiency of a positive/negative phase shift bimetallic zone plate made of two different materials is $$Eff = \frac{1}{\pi^2}[\exp(-2k\beta_1 t_1) + \exp(-2k\beta_2 t_2) - 2\exp[-k(\beta_1 t_1 + \beta_2 t_2)]\cos[k(\delta_1 t_1 - \delta_2 t_2)]]$$

wherein k=2π/λ, $t_1$ and $t_2$ are thicknesses of the two materials, respectively. Therefore, we can calculate the first-order diffraction efficiency of the novel bimetallic phase zone plate, as shown in FIG. 3 (in which the thicknesses of the two metals are set to the same).

Figure 3:
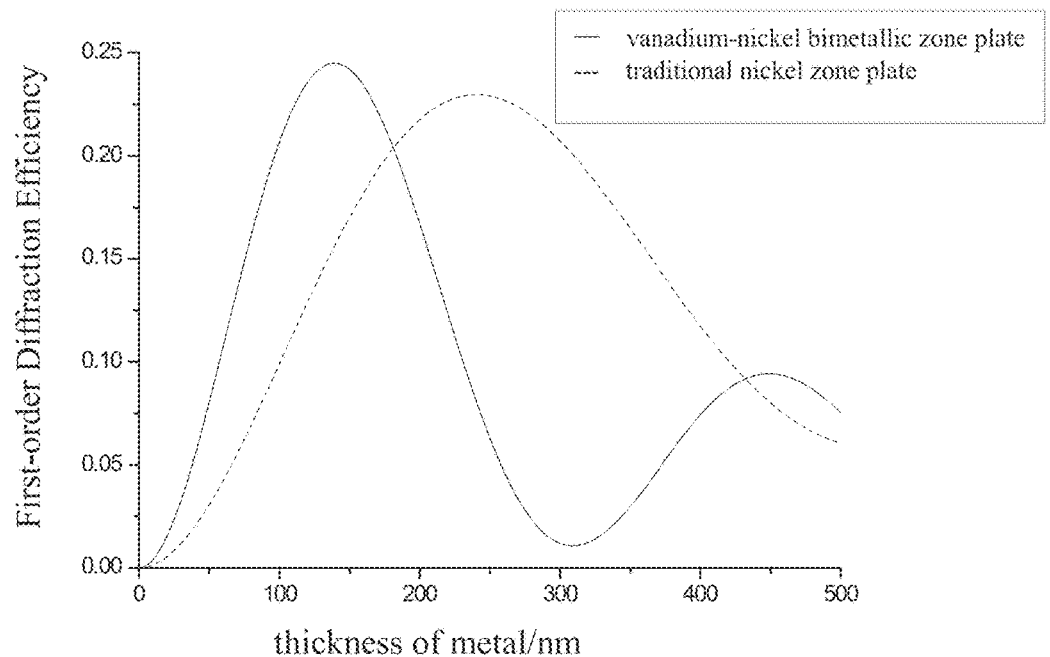
FIG. 3 shows the dependences of first-order diffraction efficiency on thickness of material in a normal nickel zone plate and a vanadium-nickel bimetallic zone plate, when the enemy is 511.9 eV.

In FIG. 3, the broken line is the first-order diffraction efficiency of a normal nickel phase zone plate, while the solid line is the first-order diffraction efficiency of a novel vanadium-nickel bimetallic phase zone plate, in which the metal thicknesses of vanadium and nickel are the same. As can be seen from above, the solution used in the invention can reduce the metal thickness in a zone plate by about a half. Additionally, in the case that the ring heights are the same (less than 150 nm), the solution used in the invention can greatly improve the diffraction efficiency of a zone plate. For example, when a zone plate has an outermost zone width of 13 nm and a ring height of 35 nm, a novel bimetallic zone plate increase the diffraction efficiency to 4.3%, from 1.6% for a normal zone plate.

Since a negative phase shift coefficient only exists in a narrow energy section for a metal, the novel phase-shift zone plate proposed by the invention can be used only at certain energies. However, in most cases for X-ray imaging, it necessary to observe the sample at only one energy, and there is not any too restrict requirement for this energy. For example, imaging of a water-containing cell in the "water window" wave range usually uses an arbitrary energy around 500 eV, such as at 520 eV, as well as at 511.9 eV, which does not notably affect the result of the imaging. In view of the above, the novel phase-shift zone plate proposed by the invention will not be restricted due to the precondition that it can be used only at certain energies.

Figure 4:
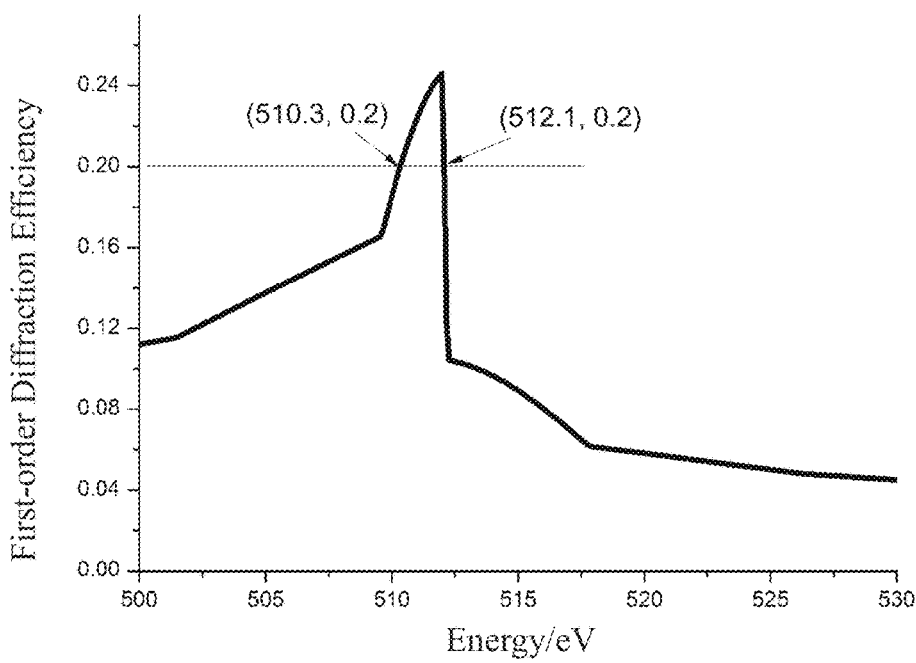
FIG. 4 shows the dependence of first-order diffraction efficiency on energy in a vanadium-nickel bimetallic zone plate, when the thickness is 140 nm.

FIG. 4 shows the dependence of the first-order diffraction efficiency of the vanadium-nickel bimetallic zone plate on the energy, when the thickness is 140 nm. As can be seen from FIG. 4, when the thickness is 140 nm, and the energy is between 510.3 and 512.1 eV, the first-order diffraction efficiency of the novel zone plate made of vanadium and nickel is above 20%. In a synchrotron radiation microscopic imaging system, energy dispersion is generally better than the order of 0.1 eV. For example, BL08U beamlines station of Shanghai Synchrotron Radiation Facility has an energy range of 250 to 2500 eV, and a resolving power of energy (E/ΔE) of 2500 to 6000. U41-FSGM beamlines station of BESSY II of Germany has an energy range of 250 to 1500 eV, and a resolving power of energy (E/ΔE) up to 10000. That is to say, a synchrotron radiation X-ray imaging system can meet the precision requirement of 1 to 2 eV for the working energy.

Additionally, the first-order diffraction efficiencies of a normal nickel zone plate and a titanium-nickel bimetallic zone plate are calculated at an energy of 453.6 eV, and the results show that the thickness can be reduced from 210 nm to 130 nm, while the maximum first-order diffraction efficiency almost does not change. Furthermore, for a zone plate having an outermost zone width of 13 nm and a ring height of 35 nm, the novel titanium-nickel bimetallic zone plate increases the efficiency to 4.6%, from 2.0% for a normal zone plate.

A processing technique useful for processing a positive/negative phase shift bimetallic zone plate is provided below (taking vanadium-nickel bimetallic one having a thickness of 100 nm as example):

1. depositing metal vanadium thin film having a thickness of 100 nanometers on a silicon nitride substrate by ion beam sputtering;
2, spin coating an electron beam photoresist PMMA having a thickness of 400 nanometers, drying at 180 degree;
3. performing electron beam exposure, to form a zone plate nanostructure;
4. transferring the zone plate structure to a metal thin film by using ion beam etching, to form a metal vanadium zone plate structure; argon ion etching, energy: 500 eV, beam flow density: 0.5 mA/cm$^2$;
5, depositing a metal nickel thin film having a thickness of 100 nanometers on the sample by using ion beam sputtering;
6. immersing the sample in acetone, to remove the photoresist t or a zone plate structure having alternate metals vanadium and nickel;
7. opening a window at the back side of the sample (30% KOH, 80° C.), to obtain a zone plate having alternate metals vanadium and nickel and a thickness of 100 nanometers.

The invention claimed is:

1. A positive/negative phase shift bimetallic zone plate; comprising:
    a first metallic material having a positive phase shift;
    a second metallic material having a negative phase shift at a working energy point;
    wherein the first metallic material and the second metallic material are alternately arranged, so that the second metallic material replaces the blank portion in a cycle of a traditional zone plate.

2. The positive/negative phase shift bimetallic zone plate of claim 1, wherein the positive/negative phase shift bimetallic zone plate is annular, and the first metallic material and the second metallic material form a structure of alternate rings.

3. The positive/negative phase shift bimetallic zone plate of claim 1, the first metallic material is selected from nickel, gold, germanium, titanium, vanadium, chromium, manganese, iron, copper, zinc.

4. The positive/negative phase shift bimetallic zone plate of claim 1, the second metallic material is selected from titanium, vanadium, chromium, manganese, iron, cobalt, nickel, copper, zinc, gallium, germanium, hafnium, tungsten, rhenium and osmium.

5. The positive/negative phase shift bimetallic zone plate of claim 1, wherein in the case that the positive/negative phase shift bimetallic zone plate has the same thickness as that of a normal monometallic phase zone plate, the diffraction efficiency of the positive/negative phase shift bimetallic zone plate is higher than the diffraction efficiency of the normal monometallic phase zone plate in conventional ranges.

6. The positive/negative phase shift bimetallic zone plate of claim 1, the positive/negative phase shift bimetallic zone plate is a vanadium-nickel, titanium-nickel, or vanadium-gold bimetallic zone plate.

7. A method of producing a positive/negative phase shift bimetallic zone plate, comprising following steps:
   a. depositing a thin film of a first metallic material on a substrate;
   b. forming a photoresist having a zone plate structure on the thin film of the first metallic material;
   c. transferring the zone plate structure to the thin film of the first metallic material by performing etching via the formed photoresist having the zone plate structure, so as to form a zone plate structure of the first metallic material;
   d. depositing the second metallic material at interspaces formed by the etching;
   e. removing the photoresist, so as to form a positive/negative phase shift bimetallic zone plate structure.

8. The method of claim 7, wherein the photoresist is coated by spin coating, and thereafter is subjected to electron beam exposure
   or interference lithography, so as to form a photoresist having a zone plate structure.

9. The method of claim 7, wherein the etching in step d is performed by argon ion etching or reactive ion etching.

10. The method of claim 7, further comprising:
   opening a window on the back side of the positive/negative phase shift bimetallic zone plate structure obtained in step e, to obtain the positive/negative phase shift bimetallic zone plate.

* * * * *